United States Patent
Noguchi

(10) Patent No.: US 10,221,389 B2
(45) Date of Patent: Mar. 5, 2019

(54) METHOD OF PRODUCING CELL POPULATION WITH HIGH TARGET CELL PURITY

(71) Applicant: TERUMO KABUSHIKI KAISHA, Shibuya-ku, Tokyo (JP)

(72) Inventor: Eri Noguchi, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 44 days.

(21) Appl. No.: 15/230,788

(22) Filed: Aug. 8, 2016

(65) Prior Publication Data
US 2016/0340643 A1 Nov. 24, 2016

Related U.S. Application Data

(63) Continuation of application No. PCT/JP2015/055467, filed on Feb. 25, 2015.

(30) Foreign Application Priority Data

Feb. 26, 2014 (JP) .................................. 2014-035358

(51) Int. Cl.
| | |
|---|---|
| C12N 5/00 | (2006.01) |
| A61K 35/28 | (2015.01) |
| A61K 35/34 | (2015.01) |
| A61L 27/38 | (2006.01) |
| C12N 5/077 | (2010.01) |

(52) U.S. Cl.
CPC ............ *C12N 5/0081* (2013.01); *A61K 35/28* (2013.01); *A61K 35/34* (2013.01); *A61L 27/3834* (2013.01); *C12N 5/0658* (2013.01)

(58) Field of Classification Search
CPC combination set(s) only.
See application file for complete search history.

(56) References Cited

U.S. PATENT DOCUMENTS

| | | | |
|---|---|---|---|
| 5,284,766 | A | 2/1994 | Okano et al. |
| 2004/0048778 | A1 | 3/2004 | Druggan |
| 2007/0092492 | A1 | 4/2007 | Matsuda et al. |
| 2009/0053277 | A1 | 2/2009 | Nagaya et al. |
| 2014/0072599 | A1 | 3/2014 | Kinooka et al. |
| 2016/0067284 | A1 | 3/2016 | Sakamoto et al. |

FOREIGN PATENT DOCUMENTS

| | | |
|---|---|---|
| EP | 2 682 134 A1 | 1/2014 |
| JP | 2-211865 A | 8/1990 |
| JP | 2003-033177 | 2/2003 |
| JP | 2003-33177 A | 2/2003 |
| JP | 2004-508824 A | 3/2004 |
| JP | 2007-89442 A | 4/2007 |
| JP | 2007-528755 A | 10/2007 |
| JP | 2010-081829 | 4/2010 |
| JP | 2010-81829 A | 4/2010 |
| JP | 2010-226962 | 10/2010 |
| JP | 2010-226962 A | 10/2010 |
| JP | 2010/226991 A | 10/2010 |
| JP | 2011-110368 A | 6/2011 |
| JP | 2011-115058 | 6/2011 |
| JP | 2011-115058 A | 6/2011 |
| JP | 2011-172925 | 9/2011 |
| JP | 2011-172925 A | 9/2011 |
| JP | 2012/44970 A | 3/2012 |
| WO | WO 2005/011524 A1 | 2/2005 |
| WO | WO 2006/080434 A1 | 3/2006 |
| WO | WO 2012/118099 A1 | 9/2012 |
| WO | WO 2014/185517 A1 | 11/2014 |

OTHER PUBLICATIONS

Agley et al "Human skeletal muscle fibroblasts, but not myogenic cells, readily undergo adipogenic differentiation." J Cell Science, 2013, vol. 126, pp. 5610-5625. (Year: 2013).*
Konigsberg LR: Skeletal myoblasts in culture. In: Methods in Enzymology. Jakoby W.B., Paston I.H. (eds), Academic Press, New York, 1979, pp. 511-527. (Year: 1979).*
International Search Report (PCT/ISA/210) dated May 26, 2015, by the Japanese Patent Office as the International Searching Authority for International Application No. PCT/JP2015/055467.
Extended European Search Report dated May 15, 2017 in corresponding European Application No. 15754953.6.
Dr. Michael Rieger, "Cell Separation Methods", Georg Speyer Haus, Jan. 1, 2012, pp. 1-32.
D. Lamosova et al., "In vitro Separation of Embryonic Chick Skeletal Muscle Myoblasts and Fibroblasts: Comparison of Their Characteristics", Physiol. Res. 43, 1994, pp. 157-161.
Terry E. Thomas et al., "Purification of Hematopoietic Stem Cells for Further Biological Study", Methods: A Companion to Methods in Enzymology 17, 1999, pp. 202-218.

(Continued)

*Primary Examiner* — Allison M Fox
(74) *Attorney, Agent, or Firm* — Buchanan Ingersoll & Rooney PC

(57) ABSTRACT

A method is disclosed of producing a cell population with a high target cell purity, including changing a character of contaminating cells in a cell population including target cells and the contaminating cells, and removing the contaminating cells and/or collecting the target cells based on the changed character. The disclosure also relates to a cell population with a high target cell purity, produced by the method, and a method of producing a sheet-shaped cell culture, including culturing the cell population into a sheet shape, a sheet-shaped cell culture containing the cell population, a medical composition containing an effective component selected from the group including the cell population and the sheet-shaped cell culture, and a method of treating a disease in a subject, including administering an effective amount of the cell population, the sheet-shaped cell culture or the medical composition, to the subject needing the same.

9 Claims, 1 Drawing Sheet

(56) References Cited

OTHER PUBLICATIONS

Christine Vaculik et al., "Human Dermis Harbors Distinct Mesenchymal Stromal Cell Subsets", Journal of Investigative Dermatology, vol. 132, No. 3, Part 1, Mar. 1, 2012, pp. 563-574.
Mirko Corselli et al., "Identification of Perivascular Mesenchymal Stromal/Stem Cells by Flow Cytometry", Cytometry Part A, vol. 83, No. 1, Aug. 1, 2013, pp. 714-720.
Feng R. et al."PU.1 and C/EBPalpha/beta convert fibroblasts into macrophage-like cells.", Proc Natl Acad Sci U S A., Apr. 22, 2008, vol. 105, No. 16, pp. 6057-6062. (Abstract only).
Freytag S. O. et al.,"Ectopic expression of the CCAAT/enhancer-binding protein α promotes the adipogenic program in a variety of mouse fibroblastic cells", Genes & Development, 1994, vol. 8, pp. 1654-1663.
Haraguchy Y. et al.,"Concise Review: Cell Therapy and Tissue Engineering for Cardiovascular Disease", Stem Cells Translational Medicine, 2012, vol. 1, pp. 136-141.
Huang P. et al.,"Induction of functional hepatocyte-like cells from mouse fibroblasts by defined factors" Nature. May 11, 2011, vol. 475, No. 7356, pp. 386-389.
Kim J. B. et al.,"ADD 1/SREBP1 promotes adipocyte differentiation and gene expression linked to fatty acid metabolism", Genes& Development, May 1, 1996, vol. 10, pp. 1096-1107.
Marcucci F et al.,"Active targeting with particulate drug carriers in tumor therapy: fundamentals and recent progress", Drug Discov Today, Mar. 1, 2004, vol. 9, No. 5, pp. 219-228. (Abstract only).
Nizzardo M. et al.,"Direct reprogramming of adult somatic cells into other lineages: past evidence and future perspectives", Cell Transplant., 2013, vol. 22, No. 6, pp. 921-944. (Abstract only).
Sekiya S. et al.,"Direct conversion of mouse fibroblasts to hepatocyte-like cells by defined factors", Nature. Jun. 29, 2011, vol. 475, No. 7356, pp. 390-393. (Abstract only).
Tontonoz P. et al."Stimulation of adipogenesis in fibroblasts by PPAR gamma 2, a lipidactivated transcription factor", Cell., Dec. 30, 1994, vol. 79, No. 7, pp. 1147-1156. (Abstract only).
Zhu J. et al.,"Direct conversion of porcine embryonic fibroblasts into adipocytes by chemical molecules",Cell Reprogram, Apr. 14, 2012, vol. 2, pp. 99-105. (Abstract only).
Arauchi A. et al.,"Tissue-engineered thyroid cell sheet rescued hypothyroidism in rat models after receiving total thyroidectomy comparing with nontransplantation models",Tissue Eng Part A., Dec. 15, 2009, vol. 12, pp. 3943-3949. (Abstract only).
Bou-Gharios G. et al.,"A potent far-upstream enhancer in the mouse pro alpha 2(I) collagen gene regulates expression of reporter genes in transgenic mice", J Cell Biol., Sep. 1996, vol. 134, No. 5, pp. 1333-1344. (Abstract only).
Goodpaster T. et al.,"An immunohistochemical method for identifying fibroblasts in formalin-fixed, paraffin-embedded tissue", J Histochem Cytochem., Apr. 2008, vol. 56, No. 4), pp. 347-358, Epub Dec. 10, 2007. (Abstract only).
Ito A. et al.,"Construction and delivery of tissue-engineered human retinal pigment epithelial cell sheets, using magnetite nanoparticles and magnetic force", Tissue Eng., Mar.-Apr. 2005, vol. 11, No. 3-4, pp. 489-496. (Abstract only).
Iwahana H. et al."Different promoter usage and multiple transcription initiation sites of the interleukin-1 receptor-related human ST2 gene in UT-7 and TM12 cells", Eur J Biochem., Sep. 1999, vol. 264, No. 2, pp. 397-406. (Abstract only).
Lu N. et al.,"The human alpha11 integrin promoter drives fibroblast-restricted expression in vivo and is regulated by TGF-beta1 in a Smad- and Sp1-dependent manner", Matrix Biol., Apr. 2010, vol. 29, No. 3, pp. 166-176, Epub Nov. 12, 2009. (Abstract only).
Okada H. et al.,"Identification of a novel cis-acting element for fibroblast-specific transcription of the FSP1 gene", Am J Physiol., Aug. 1998, vol. 275, No. 2, Pt .2, pp. 306-314. (Abstract only).
Rosendaal M. et al.,"Up-regulation of the connexin43+ gap junction network in haemopoietic tissue before the growth of stem cells", J Cell Sci., Jan. 1994, vol. 107, Pt 1, pp. 29-37. (Abstract only).
Torchilin VP.,"Drug targeting", Eur J Pharm Sci., Oct. 2000, vol. 11, Suppl. 2, pp. S81-S91. (Abstract only).
Yaji N. et al.,"Transplantation of tissue-engineered retinal pigment epithelial cell sheets in a rabbit model", Biomaterials., Feb. 2009, vol. 30, No. 5, pp. 797-803, Epub Nov. 25, 2008. (Abstract only).
Ebihara G. et al.,"Cartilage repair in transplanted scaffold-free chondrocyte sheets using a minipig model", Biomaterials., May 2012, vol. 33, No. 15, pp. 3846-3851, Epub Feb. 25, 2012. (Abstract only).
Shimizu H. et al.,"Bioengineering of a functional sheet of islet cells for the treatment of diabetes mellitus", Biomaterials., Oct. 2009, vol. 30, No. 30, pp. 5943-5949, Epub Aug. 11, 2009. (Abstract only).
Takagi R. et al.,"Cell sheet technology for regeneration of esophageal mucosa", World J Gastroenterol., Oct. 7, 2012, vol. 18, No. 37, pp. 5145-5150. (Abstract only).
Wang CC. et al.,"Direct intramyocardial injection of mesenchymal stem cell sheet fragments improves cardiac functions after infarction", Cardiovasc Res., Feb. 1, 2008, vol. 77, No. 3, 515-524. Epub Oct. 19, 2007. (Abstract only).
Watanabe E. et al.,"Bladder augmentation using tissue-engineered autologous oral mucosal epithelial cell sheets grafted on demucosalized gastric flaps", Transplantation., Apr. 15, 2011, vol. 91, No. 7, pp. 700-706. (Abstract only).
Yaguchi Y. et al.,"Middle ear mucosa regeneration by grafting of artificial mucosa", Acta Otolaryngol., Oct. 2007, vol. 127, No. 10, 1038-1044. (Abstract only).
Lecourt et al., "Characterization of distinct mesenchymal-like cell populations from human skeletal muscle in situ and in vitro," Experimental Cell Research, (Sep. 10, 2010), vol. 316, No. 15, pp. 2513-2526.
Office Action (Communication pursuant to Article 94(3) EPC) dated Aug. 13, 2018, by the European Patent Office in corresponding European Patent Application No. 15 754 953.6-1112. (6 pages).
Notification of Reasons for Refusal dated Nov. 5, 2018 in corresponding Japanese Patent Application No. 2016-505272, and an English translation thereof.

* cited by examiner

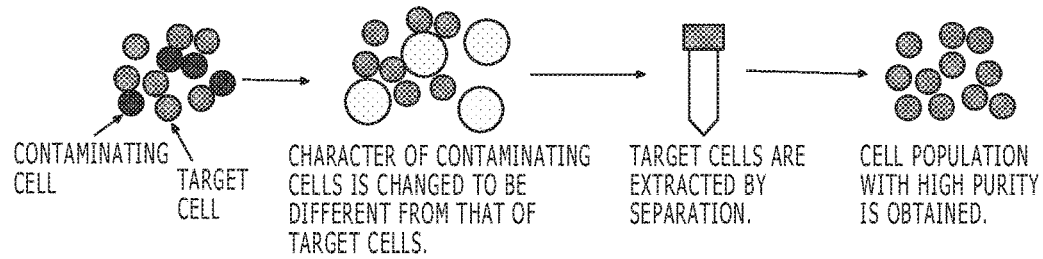

METHOD OF PRODUCING CELL POPULATION WITH HIGH TARGET CELL PURITY

CROSS-REFERENCES TO RELATED APPLICATIONS

This application is a continuation of International Application No. PCT/JP2015/055467 filed on Feb. 25, 2015, which claims priority to JP 2014-035358 filed on Feb. 26, 2014, the entire contents of which are incorporated herein by reference.

TECHNICAL FIELD

The present disclosure relates to a method of producing a cell population with a high target cell purity, a cell population obtained by the method, and a medical composition containing the cell population.

BACKGROUND

In recent years, attempts to transplant various cells have been conducted in order to repair injured tissue. For instance, for repairing cardiac muscle tissue injured due to ischemic cardiopathy such as stenocardia and myocardial infarction, attempts have been made to utilize fetal cardiac muscle cells, skeletal myoblasts, mesenchymal stem cells, cardiac stem cells, and ES cells. (See Haraguchi et al., Stem Cells Transl Med. 2012 February; 1(2): 136-41).

As part of such attempts, cell structures formed by utilizing a scaffold and sheet-shaped cell cultures obtained by forming cells in a sheet shape have been developed (See JP-T-2007-528755).

In regard of application of a sheet-shaped cell culture to therapy, investigations of utilization of a cultured skin sheet for a skin injury due to burn or the like, utilization of a sheet-shaped cell culture of corneal epithelium for a corneal injury, utilization of a sheet-shaped cell culture of oral mucosa for endoscopic resection of esophageal cancer have been under way.

Cells to be used for cell transplantation are normally obtained by separating them from the subject's tissue relevant to the transplantation, in order to avoid adverse events such as rejection. In many cases, however, the tissue includes other cells than the target cells. If the cells obtained from the tissue are cultured without purification of the target cells, the other cells than the target cells are also proliferated, lowering the proportion of the target cells in the cells to be used for transplantation. However, when the other cells than the target cells are transplanted, a therapeutic effect as high as that in the case of transplantation of the target cells cannot be obtained. It may be impossible, therefore, to obtain a sufficient therapeutic effect even by transplanting the cells obtained from the tissue, if the cells to be transplanted are low in target cell purity.

As a measure to enhance the proportion of the target cells contained in a cell population separated from the tissue, there has been known, for example, a method wherein in separating skeletal myoblasts from a skeletal muscle tissue, the skeletal muscle tissue is subjected to an enzyme treatment by immersion in a proteinase solution for a predetermined time, the resulting enzyme treatment liquid is discarded, thereafter the skeletal muscle tissue is again subjected to an enzyme treatment by immersion in an proteinase solution for a predetermined time, and cells contained in the enzyme treatment liquid thus obtained are recovered (JP-A-2007-89442).

SUMMARY

A method is disclosed of producing a cell population with a high target cell purity from a cell population including target cells and contaminating cells, and more particularly a method of producing such a cell population easily and efficiently, a cell population with a high target cell purity obtained by the method, and a medical composition containing the cell population.

In accordance with an exemplary embodiment, when a character of contaminating cells in a cell population including target cells and the contaminating cells is changed, and the contaminating cells are removed and/or the target cells are collected on the basis of the changed character, a cell population can be obtained with a high target cell purity.

A method is disclosed of producing a cell population with a high target cell purity, including: changing a character of contaminating cells in a cell population including target cells and the contaminating cells; and removing the contaminating cells and/or collecting the target cells, on the basis of the changed character.

According to an exemplary embodiment, the contaminating cells are fibroblasts.

According to an exemplary embodiment, the character is selected from the group including cell shape, size, specific gravity, surface charge, adhesion potency, and marker.

According to an exemplary embodiment, the target cells are skeletal myoblasts or mesenchymal stem cells.

According to an exemplary embodiment, a cell population with a high target cell purity, produced by the method as disclosed herein.

According to an exemplary embodiment, a method of producing a sheet-shaped cell culture, which includes culturing the cell population into a sheet shape.

According to an exemplary embodiment, wherein the sheet-shaped cell culture, including the cell population as disclosed herein.

According to an exemplary embodiment, a medical composition containing an effective component selected from the group including the cell population and the sheet-shaped cell culture as disclosed herein.

According to an exemplary embodiment, the medical composition as disclosed herein for treating a disease associated with tissue abnormality.

According to an exemplary embodiment, a method of treating a disease in a subject, including administering an effective amount of the cell population, the sheet-shaped cell culture or the medical composition as disclosed herein, to the subject needing the same.

According to the present disclosure, the purity of target cells included in a cell population that is collected from a living body can be enhanced and includes a plurality of kinds of cells, to enhance the therapeutic effect of cell transplantation, and to make efficient the production of a cell composition for use in such a therapy. In addition, by selecting cell size, specific gravity, or surface charge as the character to be changed, a technique is disclosed which is simple and capable of treating a large amount of cells at a time, such as filtration and centrifugation, and whereby target cells can be efficiently purified.

A method is disclosed of producing a sheet-shaped cell culture, the method comprising: changing a character of contaminating cells in a cell population including target cells and the contaminating cells that is collected from a subject;

obtaining a cell population with a high target cell purity by removing the contaminating cells and/or collecting the target cells based on the changed character; freezing the cell population; thawing the frozen cell population; culturing the cell population into a sheet shape to form a sheet-shaped cell culture; and recovering the sheet-shaped cell culture formed.

BRIEF DESCRIPTION OF THE DRAWINGS

FIG. 1 is a diagram showing a fundamental concept of the present disclosure.

DETAILED DESCRIPTION

Unless defined otherwise herein, all the technical terms and scientific terms used herein have the same meanings as normally understood by persons skilled in the art. All the patents, patent applications, published patent applications and other publications referenced herein are quoted herein in their entireties by reference.

A method is disclosed of producing a cell population with a high target cell purity, including (1) a step of changing a character of contaminating cells in a cell population including target cells and the contaminating cells, and (2) a step of removing the contaminating cells and/or collecting the target cells based on the changed character (hereinafter the method may be referred to simply as "cell population production method").

In the present disclosure, the target cells and the contaminating cells can be arbitrarily set according, for example, to the use of the cell population obtained. Since the cell population including the target cells and the contaminating cells is typically prepared from a tissue collected from a living body, the target cells and the contaminating cells are typically selected from the cells present in the same tissue. For example, a cell population prepared from a skeletal muscle tissue is composed mainly of skeletal myoblasts and fibroblasts, one of them may be set as the target cells and the other may be set as the contaminating cells. Thus, in one embodiment of the present disclosure, the target cells are skeletal myoblasts and the contaminating cells are fibroblasts. In another embodiment of the present disclosure, the target cells are fibroblasts and the contaminating cells are skeletal myoblasts. A cell population prepared from bone marrow tissue is composed mainly of mesenchymal stem cells, hematopoietic stem cells, blood precursor cells, and fibroblasts, one or more of them may be set as the target cells, and the other or others may be set as the contaminating cells. Thus, in one embodiment of the present disclosure, examples of a setting that may be adopted include, without restriction, a setting wherein the target cells are mesenchymal stem cells and the contaminating cells are hematopoietic stem cells, blood precursor cells and fibroblasts, and a setting wherein the target cells are mesenchymal stem cells and hematopoietic stem cells and the contaminating cells are blood precursor cells and fibroblasts.

The target cells and the contaminating cells can also be selected from part of cell species present in body tissues. In other words, it is unnecessary for all the cell species present in body tissues to be classified into the target cells and the contaminating cells in the present disclosure. A method can be adopted wherein cell species that can be easily separated from the target cells without changing a character thereof are preliminarily removed by a pretreatment, and the target cells and the contaminating cells are selected from the cell species remaining after the pretreatment. Examples of the pretreatment applicable here include, without restriction, filtration (for example, filtration by filter or microchannel device), centrifugation (for example, density gradient centrifugation, isodensity centrifugation, countercurrent centrifugal elutriation (CCE), etc.), and separation between adhered cells and floating cells by adhesion culture. In accordance with an exemplary embodiment, for example, in the case of producing a cell population with a high purity of mesenchymal stem cells as target cells from bone marrow tissue, floating cells (for example, hematopoietic stem cells, blood precursor cells, hematocyte-based cells, etc.) can be removed by a pretreatment such as adhesion culture, and fibroblasts that are contained in the remaining adhered-cell population and are difficult to separate from the mesenchymal stem cells can be selected as the contaminating cells (namely, the cells whose character is to be changed) in the present disclosure. Therefore, the cell population production method of the present disclosure may further include a step of removing other cells than the target cells and the contaminating cells from a tissue collected from a living body before the step of changing the character of the contaminating cells.

In the case of using a cell population for medical use (examples thereof include, without restriction, such uses as treatment of diseases, transplantation therapy, and regenerative therapy), examples of cells from which the target cells can be selected include, without restriction, hematopoietic stem cells for use in treatment of hemopathy or the like, lymphocytes for use in immunotherapy or the like, immunocytes such as dendritic cells, cells capable of forming sheet-shaped cell cultures, for example, myoblasts (for example, skeletal myoblasts), mesenchymal stem cells (for example, those derived from bone marrow, adipose tissues, peripheral blood, skin, hair roots, muscular tissues, endometria, placentas, and cord blood), cardiac muscle cells, fibroblasts, cardiac stem cells, embryonic stem cells, synovial cells, chondrocytes, epithelial cells (for example, oral mucosal epithelial cells, retinal pigment epithelial cells, nasal mucosa epithelial cells, etc.), endothelial cells (for example, vascular endothelial cells), hepatocytes (for example, hepatic parenchymal cells), pancreatic cells (for example, pancreatic islet cells), renal cells, adrenal cells, periodontal ligament cells, gingival cells, periosteal cells, and skin cells. In this case, the contaminating cells can be selected from other cells than the target cells that are present in the tissue in which the target cells exist, particularly, those cells that are difficult to separate from the target cells and that are high in proliferation potency and/or abundance ratio in the tissue.

In one embodiment of the present disclosure, the contaminating cells are fibroblasts. In one embodiment of the present disclosure, the target cells are myoblasts, preferably skeletal myoblasts. In a preferred embodiment of the present disclosure, the target cells are skeletal myoblasts and the contaminating cells are fibroblasts. In another embodiment of the present disclosure, the target cells are mesenchymal stem cells. In a preferred embodiment of the present disclosure, the target cells are mesenchymal stem cells and the contaminating cells are fibroblasts.

As the character of the contaminating cells that is to be changed, one or more of any known characters can be selected. It can be preferable, however, that the character is a character, which, after changed, is useful for separation of the contaminating cells from the target cells. Examples of such a character include, without restriction, cell size, specific gravity, surface charge, presence/absence of marker expression, adhesion potency, proliferation potency, and chemotaxis. Changing of the character can be carried out by any known technique or a combination of such techniques.

For instance, it is known that a cell species can be converted into another cell species by introduction of a gene such as a transcription factor or by administration of a drug (for example, Nizzardo et al., Cell Transplant. 2013; 22(6): 921-44, Zhu et al., Cell Reprogram. 2012 April; 14(2): 99-105, etc.). Therefore, the step of changing a character of contaminating cells in the present disclosure includes conversion of the contaminating cells into cell species easy to separate from the target cells, the conversion being carried out by such a technique as just-mentioned.

For instance, techniques for conversion of fibroblasts into fat cells, megakaryocytes, platelets, hepatocyte-like cells, macrophage-like cells, neurons, cardiac muscle cells or the like have been known (for example, the above-mentioned Nizzardo et al., 2013, Zhu et al., 2012, Ono et al., Blood. 2012 Nov. 1; 120(18): 3812-21, etc.). Therefore, by conversion of fibroblasts as the contaminating cells into any one of these cells which are different in character from the desired target cells, for example, skeletal myoblasts or mesenchymal stem cells, the converted contaminating cells can be separated or removed from the skeletal myoblasts or mesenchymal stem cells and/or the skeletal myoblasts or mesenchymal stem cells can be separated or removed from the converted contaminating cells. For instance, while the cell diameter of skeletal myoblasts is approximately, for example, 11 to 18 µm, the cell diameter of megakaryocytes is approximately, for example, 35 to 160 µm, the cell diameter of platelets is approximately, for example, 2 to 4 µm, the cell diameter of hepatocytes is approximately, for example, 20 to 30 µm, and the cell diameter of macrophages is approximately, for example, 25 to 50 µm. When fibroblasts are converted into any of these cells, therefore, the converted cells can be separated from the skeletal myoblasts by utilizing the difference in cell size. In addition, fat cells are different from skeletal myoblasts or mesenchymal stem cells in specific gravity. When fibroblasts are converted into fat cells, therefore, the converted cells can be separated from the skeletal myoblasts or mesenchymal stem cells by utilizing the difference in cell specific gravity.

Conversion of fibroblasts into fat cells can be conducted by a method examples of which include, without restriction, introduction of such a factor as PPARγ (Tontonoz et al., Cell. 1994 Dec. 30; 79(7): 1147-56), C/EBPα (Freytag et al., Genes Dev. 1994 Jul. 15; 8(14): 1654-63) or ADD1/SREBP-1 (Kim and Spiegelman, Genes Dev. 1996 May 1; 10(9): 1096-107), and a treatment by a combination of a TGF-β signaling inhibitor (for example, TGF-β RI kinase inhibitor such as SB43152) with a ROCK signaling inhibitor (for example, Thiazovivin) (the above-mentioned Zhu et al., 2012). Conversion of fibroblasts into hepatocyte-like cells can be performed by a method, examples of which can include, without restriction, a combination of introduction of Gata4, Hnf1α and Foxa3 with inactivation of p19Arf (Huang et al., Nature. 2011 May 11; 475 (7356): 386-9), and introduction of Hnf4α together with Foxa1, Foxa2 or Foxa3 (Sekiya and Suzuki, Nature. 2011 Jun. 29; 475(7356): 390-3). Conversion of fibroblasts into macrophage-like cells can be carried out by a method, examples of which can include, without restriction, introduction of PU. 1 together with C/EBPα or C/EBPβ (Feng et al., Proc Natl Acad Sci USA. 2008 Apr. 22; 105(16): 6057-62). Conversion of fibroblasts into megakaryocytes and platelets can be conducted by a method, examples of which can include, without restriction, introduction of p45NF-E2, Maf G and Maf K (the above-mentioned Ono et al., 2012). Conversion of fibroblasts into neurons can be performed by a method, examples of which can include, without restriction, introduction of Ascl1, Brn2 and Myt1I, introduction of Ascl1, Brn2, Myt1I and NeuroD1, introduction of miR-9/9, miR-124, NeuroD2, Ascl1 and Myt1I, introduction of Mash1, Nurr1 and Lmx1a, introduction of Ascl1, Pitx3, Lmx1a, Nurr1, Foxa2 and EN1, and introduction of Ascl1, Brn2, Nyt1I, Lhx3, Hb9, Is11, Ngn2 and NEUROD1 (above-mentioned Nizzardo et al., 2013). Conversion of fibroblasts into cardiac muscle cells can be carried out by a method, examples of which can include introduction of Gata4, Tbx5 and Mef2c, and introduction of Oct4, Sox2, Klf4 and c-Myc (the above-mentioned Nizzardo et al., 2013).

Examples of other technique for changing a character of contaminating cells can include, without restriction, expression of a desired marker or inhibition of marker expression, and conversion into iPS cells and subsequent inducing of differentiation into desired cells. Examples of the desired marker include, without restriction, cell surface markers, and fluorescent proteins such as GFP. The marker expression and the inhibition of marker expression can be performed by any known technique. Examples of a marker expression technique can include introduction of a marker-coding nucleic acid into the contaminating cells. The introduction of a nucleic acid can be conducted by use of a method, examples of which can include, without restriction a calcium phosphate method, a lipofection method, an ultrasonic introduction method, an electroporation method, a particle gun method, methods based on utilization of a vector (for example, adenovirus vector, adeno-associated virus vector or retrovirus vector), and a microinjection method. Examples of a technique for inhibiting marker expression include, without restriction, an RNAi method and an antisense method. The RNAi method may include introduction of an RNAi molecule into the contaminating cells, and the antisense method may include introduction of an antisense nucleic acid into the contaminating cells.

Conversion into iPS cells can be performed, for example, by introduction of such a gene as OCT3/4, SOX2, KLF4, C-MYC, LIN28, NANOG, and GLIS1 into cells (for example, a combination of OCT3/4, SOX2, KLF4 and C-MYC, a combination of OCT3/4, SOX2, LIN28 and NANOG, a combination of OCT3/4, SOX2, KLF4 and GLIS1, a combination of OCT3/4, SOX2 and KLF4, a combination of OCT3/4 and SOX2, etc.). Methods for conversion into iPS cells have been known in the art (see, for example, Miyazaki et al., Jpn J Clin Oncol. 2012 September; 42(9): 773-9, Bayart and Cohen-Haguenauer, Curr Gene Ther. 2013 April; 13(2): 73-92), and any known conversion method or a modified method thereof can be used in the present disclosure.

Methods for conversion from iPS cells into other cell species have also been known in the art, and any known conversion method or a modified method thereof can be used in the present disclosure. Examples of a method known for conversion from iPS cells into megakaryocytes or platelets include a method wherein cells are cultivated sequentially in a culture medium containing STMspan-ACF, BMP4, VEGF and bFGF, next in a culture medium containing STEM-diff APEL Medium, TPO, SCF, Flt-3 ligand, IL-3, IL-6 and heparin, and then in a culture medium containing STEMspan-ACF, TPO, SCF, IL-6, IL-9 and heparin (Feng et al., Stem Cell Reports. 2014 Nov. 11; 3(5): 817-31). Examples of a method known for conversion from iPS cells into hepatocyte-like cells include a method wherein cells are cultivated sequentially in the presence of such factors as activin A, Wnt3, FGF4, bFGF, BMP-2, KGF, HGF, and oncostatin M (Subba Rao et al., World J Gastroenterol. 2013 Jun. 14; 19(22): 3385-96).

When used herein, an RNAi molecule refers to any molecule that provides RNA interference, and include, without restriction, double-stranded RNAs such as sRNA (small interfering RNA), miRNA (micro RNA), shRNA (short hairpin RNA), ddRNA (DNA-directed RNA), piRNA (Piwi-interacting RNA), and rasiRNA (repeat associated sRNA) and modified products thereof. These RNAi molecules are commercially available or can be designed and produced based on known sequence information. In addition, when used herein, an antisense nucleic acid includes RNA, DNA, PNA and complexes thereof.

When a nucleic acid (for example, a marker-coding nucleic acid, an RNAi molecule or a nucleic acid for coding the same) or a drug is applied to the contaminating cells, a delivery technique specific to the contaminating cells can be used. Examples of such a delivery technique include active targeting in which a targeting agent (for example, targeting ligand) specific to the contaminating cells is used (Marcucci and Lefoulon, Drug Discov Today. 2004 Mar. 1; 9(5): 219-28, Torchilin, Eur J Pharm Sci. 2000 October; 11 Suppl 2: S81-91). There are known a large number of targeting agents that are each specific to a specified cell. By the active targeting, a nucleic acid or a drug can be made to act only on the contaminating cells without acting on the target cells. Therefore, it is possible, for example, to utilize a nucleic acid or drug that produces the same effect (for example, conversion into the same cell species) on both the target cells and the contaminating cells. Examples of a targeting agent specific to fibroblasts include, without restriction, substances that bind specifically to TE-7 (refer to, for example, Rosendaal et al., J Cell Sci. 1994 January; 107(Pt 1): 29-37, Goodpaster et al., J Histochem Cytochem. 2008 April; 56(4): 347-58, and the like) which is a cell surface marker specific to fibroblasts, for example, an antibody for TE-7 or the antibody's fragments including an antigen recognition site (for example, F(ab')2, Fab', Fab, Fv, scFv fragments).

When a nucleic acid is used through expression in the contaminating cells, the nucleic acid can be placed under the control of a regulatory sequence specific to the contaminating cells, for helping ensure an expression specific to the contaminating cells. By use of such a technique, it is possible to allow expression of the nucleic acid only in the contaminating cells while inhibiting expression of the nucleic acid in the target cells. Therefore, for example, a nucleic acid can be used that produces the same effect (for example, conversion into the same cell species) on both the target cells and the contaminating cells. There are known regulatory sequences specific to a particular cell. Examples of the regulatory sequence, which can be used for nucleic acid expression specific to fibroblasts can include, without restriction, ST2 gene proximal promoter (Iwahana et al., Eur J Biochem. 1999 September; 264(2): 397-406), α11 integrin promoter (Lu et al., Matrix Biol. 2010 April; 29(3): 166-76), FSP1 gene promoter (Okada et al., Am J Physiol. 1998 August; 275(2 Pt 2): F306-14), and proα2(I) collagen enhancer (Bou-Gharios et al., J Cell Biol. 1996 September; 134(5): 1333-44). By a joint use of such a regulatory sequence with the aforementioned active targeting, the cell specificity can be further enhanced.

The character of contaminating cells to be changed may be one character or two or more characters in combination. For instance, in the case where the contaminating cells are converted into another cell species, a plurality of characters may be changed simultaneously. In addition, it is possible to effect expression of a plurality of markers or to inhibit expressions of a plurality of markers, simultaneously.

Removal of the contaminating cells or collection of the target cells can be carried out by any known technique according to the character in question. For example, in the case where the character to be changed is cell size, the removal of the contaminating cells or collection of the target cells can be performed by utilizing filtration through an appropriately sized filter (for example, nylon mesh filter) or a microchannel device or centrifugation. Where the character to be changed is cell specific gravity, the removal of the contaminating cells or collection of the target cells can be carried out by utilizing centrifugation (for example, density gradient centrifugation, isodensity centrifugation, counter-current centrifugal elutriation, etc.). Where the character to be changed is a cell surface marker, the removal of the contaminating cells or the collection of the target cells can be performed by utilizing a flow cytometry method, or an affinity separation method (for example, affinity column method, magnetic cell separation method, immunopanning, etc.). Where the character after the change is expression of a fluorescent protein, the removal of the contaminating cells or the collection of the target cells can be carried out, for example, by utilizing a flow cytometry method. Where the character to be changed is surface charge, the removal of the contaminating cells or the collection of the target cells can be performed, for example, by utilizing ion exchange chromatography, electrophoresis, or dielectrophoresis. Among these, preferred is a change of a character selected from the group including cell size, specific gravity, and surface charge, from the viewpoints of simplicity of the purifying operation and the largeness of the amount of cells that can be purified at a time.

The above-mentioned technique may be applied once or may be applied multiple times, for the same sample. In addition, where two or more techniques are present for the same character, only one of the characters may be applied, or two or more characters may be applied in combination. Furthermore, where a plurality of characters to be changed are present, removal of the contaminating cells or collection of the target cells may be performed while paying attention to one of the characters or while paying attention to two or more of the characters.

The expression "with a high target cell purity" in the present disclosure means a target cell purity higher than the target cell purity in natural tissues. For example, in the case where the target cell purity in natural tissues is, for example, 50%, the target cell purity after the method of the disclosure is carried out may be, for example, not less than 60%, not less than 65%, not less than 70%, not less than 75%, not less than 80%, not less than 85%, not less than 90%, not less than 95%, not less than 98% or not less than 99%, and most preferably 100%. The target cell purity can be determined by any known method. Examples of such a method can include a method in which the target cells are labeled with an antibody specific to the target cells, and the number of positive cells to which the antibody is bound is divided by a total number of the cells counted. The counting of the cells can be carried out by microscopic observation of a sample dyed with a specific antibody, image analysis of a microscopic image, or flow cytometric analysis of a cell population dyed with a specific antibody. In the case where the target cells are skeletal myoblasts, examples of a marker specific to the cell include, without restriction, CD56, α7 integrin, myosin heavy chain IIa, myosin heavy chain IIb, myosin heavy chain IId (IIx), MyoD, MyfS, and myogenin. Where the target cells are mesenchymal stem cells, examples of a marker specific to the cell can include, without restriction, CD29, CD73, CD90, CD105, and CD166.

The cell population production method of the present disclosure may further include a step of culturing the collected target cells and a step of subculturing the cultured cells. The cell cultivation and subculture can be carried out by use of any known method. In addition, the cell population production method of the present disclosure may further include a step of introducing a gene into the collected cells. The gene to be introduced is not particularly limited so long as the gene is useful for therapy of a disease to be treated, and may be, for example, a cytokine such as HGF. The introduction of a gene can be performed by use of any known method such as a calcium phosphate method, a lipofection method, an ultrasonic introduction method, an electroporation method, a particle gun method, methods utilizing a vector such as adenovirus vector, retrovirus vector, etc., and a microinjection method.

Another aspect of the present disclosure relates to a cell population with a high target cell purity produced by the cell population production method of the present disclosure (hereinafter this cell population may be referred to simply as "high-purity cell population"). The high-purity cell population of the present disclosure is obtained by the cell population production method of the present disclosure, and has a high target cell purity. The extent to which the target cell purity is high is as described above. The high-purity cell population of the present disclosure can include the target cells in a high proportion and is therefore useful as a source of cells for use in medical use or the like. The high-purity cell population of the present disclosure is preferably aseptic. In addition, the high-purity cell population of the present disclosure may be in adhesion to a culture vessel, may be floating in a liquid that is physiologically acceptable, or may be in a cryopreserved state.

A further aspect of the present disclosure relates to a method of producing a sheet-shaped cell culture that can include a step of culturing the high-purity cell population of the present disclosure in a sheet shape (hereinafter, the method may be referred to simply as "sheet-shaped cell culture production method").

In the present disclosure, the "sheet-shaped cell culture" refers to a cell culture in which cells are interconnected to form a sheet-shaped body, and is typically one composed of a single cell layer, but includes those composed of two or more cell layers. The cells may be interconnected directly (inclusive of the case where the cells are interconnected through a cell element such as an adhesion molecule) and/or through an intermediate substance. The intermediate substance is not specifically restricted so long as it is a substance capable of interconnecting the cells at least physically (mechanically). The intermediate substance may be, for example, an extracellular matrix. The intermediate substance is preferably one derived from cells, particularly one derived from the cells constituting the sheet-shaped cell culture. While the cells are interconnected at least physically (mechanically), they may further be interconnected functionally, for example, chemically or electrically.

The sheet-shaped cell culture of the present disclosure preferably does not include a scaffold (support), from the viewpoint of high biocompatibility and a high therapeutic effect. A scaffold is sometimes used in this technical field for adhering cells onto a surface thereof and/or to the inside thereof in order to maintain physical integrity of the sheet-shaped cell culture, and known examples of the scaffold include films made of polyvinylidene difluoride (PVDF). However, the sheet-shaped cell culture of the present disclosure preferably can maintain its physical integrity even without such a scaffold. The sheet-shaped cell culture of the present disclosure, preferably, is composed only of a substance or substances derived from the cells constituting the sheet-shaped cell culture, and does not include other substances.

The step of culturing the high-purity cell population of the present disclosure in a sheet shape can be performed by any known technique. Examples of such a technique include, without restriction, those described in Patent Document 1, JP-A-2010-081829, JP-A-2010-226962, JP-A-2010-226991, JP-A-2011-110368, JP-A-2011-115058, and JP-A-2011-172925. The step of culturing the high-purity cell population in a sheet shape may include a step of seeding the cell population to a culture substrate and a step of culturing the seeded cell population into a sheet shape.

The culture substrate is not particularly limited so long as the cell population can form a sheet-shaped cell culture on the culture substrate. Examples of the culture substrate include vessels formed from various materials, and solid or semisolid surfaces in the vessels. The vessel preferably has such a structure and material that liquid such as a culture liquid is not permeated therethrough. Examples of such a material include, without restriction, polyethylene, polypropylene, Teflon®, polyethylene terephthalate, polymethyl methacrylate, nylon 6,6, polyvinyl alcohol, cellulose, silicon, polystyrene, glass, polyacrylamide, polydimethylacrylamide, and metals (for example, iron, stainless steel, aluminum, copper, brass). In addition, the vessel preferably has at least one flat surface. Examples of such a vessel include, without restriction, cell culture dishes, and cell culture bottles. In addition, the vessel may have a solid or semisolid surface in the inside thereof. Examples of the solid surface include plates and vessels of such materials as above-mentioned, and examples of the semisolid surface include gels and soft polymer matrixes. The culture substrate may be produced by use of the above-mentioned material, or a commercially available culture substrate may be utilized. Examples of a preferable culture substrate include, without restriction, those substrates having adhesive surfaces suited to formation of the sheet-shaped cell culture thereon. Specific examples include substrates having hydrophilic surfaces such as the substrates whose surfaces are coated with corona discharge-treated polystyrene, collagen gel or a hydrophilic compound such as a hydrophilic polymer, and, further, substrates whose surfaces are coated with an extracellular matrix such as collagen, fibronectin, laminin, vitronectin, proteoglycan, glycosaminoglycan, etc. or a cell adhesion factor such as cadherin family, selectin family, integrin family, etc. Such substrates are commercially available (for example, Corning® TC-Treated Culture Dish, Corning).

The culture substrate may have a surface thereof coated with a material whose property is varied in response to a stimulus, for example, temperature or light. Examples of materials which can be used as such a material include, without restriction, known temperature-responsive materials composed of homopolymer or copolymer of (meth)acrylamide compounds, N-alkyl-substituted (meth)acrylamide derivatives (for example, N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N-ethoxyethylacrylamide, N-ethoxyethylmethacrylamide, N-tetrahydrofurfurylacrylamide, N-tetrahydrofurfurylmethacrylamide, etc.), N,N-dialkyl-substituted (meth)acrylamide derivatives (for example, N,N-dimethyl(meth)acrylamide, N,N-ethylmethylacrylamide, N,N-diethylacrylamide, etc.), (meth)acrylamide derivatives having a cyclic group (for example, 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine, 4-(1-oxo-2-methyl-2-propenyl)-morpholine, etc.), or vinyl ether derivatives (for example, methyl vinyl ether), and known photoresponsive materials such as light-absorbing polymers having an azobenzene group, copolymers of a vinyl derivative of triphenylmethane leucohydroxide with an acrylamide monomer, and N-isopropylacrylamide gel containing spirobenzopyran (refer to, for example, JP-A-2-211865, JP-A-2003-33177). By giving a predetermined stimulus to these materials, it is possible to change, for example, the hydrophilicity or hydrophobicity of the material and thereby to promote exfoliation of the sheet-shaped cell culture adhered onto the material. Culture dishes coated with a temperature-responsive material are commercially available (for example, UpCell® from Cell-Seed Inc.), and these dishes can be used in the production method of the present disclosure.

The seeding of the cell population to the culture substrate can be performed by any known technique and under any known conditions. The seeding of the cell population to the culture substrate may be conducted, for example, by injecting into a culture substrate (culture vessel) a cell suspension obtained by suspending the cell population in a culture liquid. For injection of the cell suspension, there can be used an instrument suited to a cell suspension injecting operation, such as a dropping pipette or a pipette.

The step of culturing the seeded cell population into a sheet shape can also be carried out by any known technique and under any known conditions. Nonlimitative examples of such a technique are described in Patent Document 1, JP-A-2010-081829, JP-A-2010-226962, JP-A-2010-226991, JP-A-2011-110368, JP-A-2011-115058, and JP-A-172925. Culturing the cell population into a sheet shape is considered to be achieved by adhesion of cells to one another through an intercellular adhesion mechanism such as adhesion molecules and an extracellular matrix. Therefore, the step of culturing the seeded cells into a sheet shape can be achieved, for example, by culturing the cell population under a condition where intercellular adhesion is formed. Such a condition may be any one that enables formation of intercellular adhesion; normally, intercellular adhesion can be formed in the same conditions as general cell cultivation conditions. A person skilled in the art can select an optimum condition according to the kind of the cell population seeded. Herein the cultivation for culturing the seeded cell population into a sheet shape may be referred to as "sheet-formation cultivation."

The cell culture liquid for use in cultivation (which may be referred to simply as "culture liquid" or "culture medium") is not specifically restricted so long as it can maintain the existence of cells, and, those containing amino acids, vitamins and electrolytes as main components can be utilized. As the culture liquid, there can be used a culture liquid based on a basal culture medium for cell cultivation. Examples of such a basal culture medium include, without restriction, DMEM, MEM, F12, DME, RPMI1640, MCDB (MCDB102, 104, 107, 120, 131, 153, 199, etc.), F12/DMEM, L15, SkBM, and RITC80-7. Many of these basal culture media are commercially available, and their compositions are known.

The basal culture medium may be used as is in a standard composition (for example, in an as-commercialized state) or may be used after its composition is appropriately modified according to the cell species or cell conditions. Therefore, the basal culture medium for use in the present disclosure is not limited to those of known compositions but include those obtained by addition or removal of one or more components or by increasing or decreasing the amounts of one or more components.

The cultivation of the cell population can be carried out under conditions ordinarily adopted in the technical field concerned. For example, a typical cultivation condition resides in conducting cultivation at 37° C. and 5% CO2. The cultivation can be performed in a vessel of any size and shape. The size and shape of the sheet-shaped cell culture can be arbitrarily controlled by controlling the size and shape of the cell adhesion surface of the culture vessel, or by disposing a frame of desired size and shape on the cell adhesion surface of the culture vessel and culturing the cells inside the frame.

The sheet-shaped cell culture production method of the present disclosure may further include a step of recovering the sheet-shaped cell culture. The recovery of the sheet-shaped cell culture is not particularly limited, so long as the sheet-shaped cell culture can be freed (exfoliated) from the culture substrate serving as a scaffold while maintaining its sheet structure at least partly. For example, the recovery can be carried out by an enzyme treatment using a proteinase (for example, trypsin) and/or a mechanical treatment such as pipetting. In addition, in the case where the sheet-shaped cell culture is formed by culturing a cell population on a culture substrate having a surface coated with a material whose property is varied in response to a stimulus, such as temperature or light, the sheet-shaped cell culture can be non-enzymatically freed by giving a predetermined stimulus.

A preferred embodiment of the sheet-shaped cell culture production method of the present disclosure includes the following steps:

(1) a step of changing a character of contaminating cells in a cell population including target cells and the contaminating cells that is collected from a subject;

(2) a step of obtaining a cell population with a high target cell purity by removing the contaminating cells and/or collecting the target cells based on the changed character;

(3) a step of freezing the cell population;

(4) a step of thawing the frozen cell population;

(5) a step of culturing the cell population into a sheet shape to form a sheet-shaped cell culture; and (6) a step of recovering the sheet-shaped cell culture formed.

The steps of (1), (2), (5) and (6) are the same as described above. In the above embodiment, the target cells are preferably myoblasts (particularly, skeletal myoblasts) or mesenchymal stem cells, and the contaminating cells are preferably fibroblasts.

The step (3) can be carried out by any known technique. Examples of such a technique include, without restriction, serving the cell population in a vessel to freezing means, for example, a freezer, a deep freezer, or a low-temperature medium (for example, liquid nitrogen). The temperature of the freezing means is not particularly limited, so long as it is a temperature at which part of the cell population in the vessel, preferably the whole of the cell population, can be frozen. Typically, the temperature is, for example, 0° C. or below, preferably −20° C. or below, more preferably −40° C. or below, and further preferably −80° C. or below. In addition, the cooling rate in the freezing operation is not particularly limited, so long as the cooling rate does not largely impair the survival rate or functions of the cells upon freezing and thawing. Typically, the cooling rate is such that cooling from, for example, 4° C. to −80° C. takes one to five hours, preferably two to four hours, and more particularly approximately three hours. Specifically, the cooling can be performed at a rate of, for example, 0.46° C./minute. Such a cooling rate can be achieved by a method wherein the vessel containing the cell population is served, either directly or in the state of being contained in a freezing treatment vessel, to the freezing means set at a desired temperature. The freezing treatment vessel may have a function to control the lowering rate of the temperature inside the vessel to a predetermined rate. As such a freezing treatment vessel, there can be used any known one, for example, BICELL® (Nihon Freezer Co., Ltd.).

The freezing operation may be conducted with the cell population kept immersed in a culture liquid or a physiological buffer solution. In addition, the freezing operation may be performed after a treatment such as addition of a cryoprotective agent for protecting the cells from freezing and thawing operations to the culture liquid, or replacement of the culture liquid with a cryopreservation liquid containing a cryoprotective agent. Therefore, the sheet-shaped culture production method of the present disclosure may further include a step of adding a cryoprotective agent to a culture liquid, or a step of replacing the culture liquid with a cryopreservation liquid. In the case of replacing the culture liquid with the cryopreservation liquid, the cryopreservation liquid may be added after removing the culture liquid substantially completely or may be added while part of the culture liquid is kept remaining, if the cryoprotective agent is contained in an effective concentration in the liquid in which the cells are immersed at the time of freezing. Here, the "effective concentration" means a concentration at which the cryoprotective agent, while showing no toxicity, shows a cryoprotective effect, for example, an effect of inhibiting a lowering in the survival rate, vitality, functions or the like of the cells upon freezing and thawing, as compared to the case of not using the cryoprotective agent. Such a concentration is known to persons skilled in the art, or can be appropriately determined through routine experiments.

The cryoprotective agent is not specifically restricted, so long as it shows a cryoprotective effect on cells. Examples of the cryoprotective agent include dimethyl sulfoxide (DMSO), glycerol, ethylene glycol, propylene glycol, sericin, propanediol, dextran, polyvinyl pyrrolidone, polyvinyl alcohol, hydroxyethyl starch, chondroitin sulfate, polyethylene glycol, formamide, acetamide, adonitol, perseitol, raffinose, lactose, trehalose, sucrose, and mannitol. The cryoprotective agents may be used either singly or in combination of two or more of them.

The addition concentration of the cryoprotective agent added to the culture liquid or the concentration of the cryoprotective agent in the cryopreservation liquid is not particularly limited, so long as the concentration is the effective concentration as defined above. Typically, the concentration is, for example, 2 to 20% (v/v) to the whole part of the culture liquid or the cryopreservation liquid. However, those alternative use concentrations which fall out of this concentration range but which are known for the respective cryoprotective agents or are determined empirically can also be adopted. Such alternative concentrations are also within the scope of the present disclosure.

The step (4) can be performed by any known cell thawing means. Typically, the step (4) can be achieved, for example, by a method wherein the frozen cell population is served to thawing means, for example, a solid, liquid or gaseous medium (for example, water), a water bath, an incubator, or a thermostat at a temperature higher than the freezing temperature, or by a method wherein the frozen cell population is immersed in a medium (for example, culture medium) at a temperature higher than the freezing temperature, these methods being non-limitative. The temperature of the thawing means or the immersion medium is not particularly limited, so long as it is a temperature at which the cell population can be thawed within a desired period of time. Typically, for example, the temperature is 4° C. to 50° C., preferably 30° C. to 40° C., and more preferably 36° C. to 38° C. In addition, the thawing time is not specifically restricted so long as it does not largely impair the survival rate or functions of the cells upon thawing. The thawing time is typically within, for example, two minutes; particularly, when the thawing time is within 20 seconds, lowering in the survival rate or functions can be largely restrained. The thawing time can be controlled, for example, by changing the temperature of the thawing means or immersion medium, the volume or composition of the culture liquid or cryopreservation liquid at the time of freezing.

The sheet-shaped cell culture production method as above may include a step of washing the cell population, between the step (4) and the step (5). The washing of the cell population can be carried out by any known technique. Typically, the washing is achieved, for example, by suspending the cell population in a liquid (for example, a culture liquid, or a physiological buffer solution that contains, or does not contain, serum or serum component (serum albumin or the like)), subjecting the suspension to centrifugation, discarding the supernatant liquid, and recovering the precipitated cell population, this method being non-limitative. In the step of washing the cell population, such a cycle of suspension, centrifugation and recovery may be performed once or multiple times (for example, two, three, four, or five times). In one embodiment of the present disclosure, the step of washing the cell population is carried out immediately after the step (4) of thawing the frozen cell population.

In one embodiment, all the steps of the production method (inclusive of the cell population production method and the sheet-shaped cell culture production method) of the present disclosure are carried out in vitro. In another embodiment, the production method of the present disclosure includes a step which is carried out in vivo and examples of which include, without restriction, the step of collecting a cell population or a tissue as a source of a cell population from a subject. In one embodiment, all the steps of the production method of the present disclosure are carried out under aseptic conditions. In one embodiment, the production method of the present disclosure is performed in such a manner that the cell population or sheet-shaped cell culture obtained finally will be substantially aseptic. In one embodiment, the production method of the present disclosure is carried out in such a manner that the cell population or sheet-shaped cell culture obtained finally will be aseptic.

Another aspect of the present disclosure relates to a sheet-shaped cell culture containing the high-purity cell population of the present disclosure (hereinafter, such a sheet-shaped cell culture may be referred to simply as "the sheet-shaped cell culture").

The sheet-shaped cell culture of the present disclosure is high in target cell purity. The extent of highness in purity is as described above in regard of the high-purity cell population of the present disclosure. The target cells are preferably myoblasts, particularly skeletal myoblasts, or mesenchymal stem cells. The sheet-shaped cell culture of the present disclosure may be one that is produced by the sheet-shaped cell culture production method of the present disclosure. The sheet-shaped cell culture of the present disclosure is preferably aseptic. The sheet-shaped cell culture of the present disclosure contains the target cells at high purity, and, therefore, is higher in therapeutic effect or the like, as compared to sheet-shaped cell cultures, which do not contain the high-purity cell population of the present disclosure.

The high-purity cell population and sheet-shaped cell culture of the present disclosure are useful for treatment of various diseases, particularly diseases associated with tissue abnormality. In one embodiment, therefore, the high-purity cell population and sheet-shaped cell culture of the present disclosure are for use in treating diseases associated with tissue abnormality. Examples of the tissue to be treated include, without restriction, a cardiac muscle, a cornea, a retina, an esophagus, skin, a joint, cartilage, a liver, a pancreas, gingiva, a kidney, a thyroid gland, a skeletal muscle, a middle ear, and bone marrow. In addition, the diseases to be treated can include, without restriction, cardiac diseases (for example, myocardial damage (myocardial infarction, cardiac injury), cardiomyopathy, etc.), corneal diseases (for example, corneal epithelial stem cell deficiency, corneal injury (thermal/chemical corrosion), corneal ulcer, corneal clouding, corneal trepanation, corneal cicatrization, Stevens-Johnson syndrome, ocular pemphigoid, etc.), retinal diseases (for example, retinitis pigmentosa, and age-related macular degeneration, etc.), esophageal diseases (for example, prevention of inflammation or stenosis of esophagus after esophageal surgery (removal of esophageal cancer), etc.), skin diseases (for example, skin injury (traumatic injury and burn), etc.), joint diseases (for example, degenerative arthritis, etc.), cartilage diseases (for example, cartilage injury, etc.), liver diseases (for example, chronic hepatopathy, etc.), pancreatic diseases (for example, diabetes, etc.), dental diseases (for example, periodontal disease, etc.), renal diseases (for example, renal insufficiency, renal anemia, renal osteodystrophy, etc.), thyroid diseases (for example, hypothyrosis, etc.), muscular diseases (for example, muscle injury, myositis, etc.), middle ear diseases (for example, tympanitis, etc.), and bone marrow diseases (for example, leukemia, aplastic anemia, immunodeficiency disease, etc.).

That the high-purity cell population and sheet-shaped cell culture of the present disclosure are useful for the above-mentioned diseases is described in, for example, Patent Document 1, Non-patent Document 1, Arauchi et al., Tissue Eng Part A. 2009 December; 15(12): 3943-9, Ito et al., Tissue Eng. 2005 March-April; 11(3-4): 489-96, Yaji et al., Biomaterials. 2009 February; 30(5): 797-803, Yaguchi et al., Acta Otolaryngol. 2007 October; 127(10): 1038-44, Watanabe et al., Transplantation. 2011 Apr. 15; 91(7): 700-6, Shimizu et al., Biomaterials. 2009 October; 30(30): 5943-9, Ebihara et al., Biomaterials. 2012 May; 33(15): 3846-51, Takagi et al., World J Gastroenterol. 2012 Oct. 7; 18(37): 5145-50, etc.

While the high-purity cell population and sheet-shaped cell culture of the present disclosure can be applied to a tissue to be treated and can thereby be used for repairing or regenerating the tissue, they can also be transplanted to other part (for example, subcutaneous tissue) than the tissue to be treated, as a source of a biologically active agent such as hormone (for example, Arauchi et al., Tissue Eng Part A. 2009 December; 15(12): 3943-9, Shimizu et al., Biomaterials. 2009 October; 30(30): 5943-9, etc.). In addition, the sheet-shaped cell culture of the present disclosure can be fragmented to an injectable size and the sheet-shaped cell culture can be injected into a part needing a treatment (Wang et al., Cardiovasc Res. 2008 Feb. 1; 77(3): 515-24).

The high-purity cell population and sheet-shaped cell culture of the present disclosure may further contain various additive components, examples of which include a carrier that is pharmaceutically acceptable, components for enhancing the viability, engrafting property and/or functions of the high-purity cell population and/or sheet-shaped cell culture, and other effective components useful for treatment of the disease to be treated. As such additive components, there can be used any known ones, and persons skilled in the art are well informed about these additive components. In addition, the high-purity cell population and sheet-shaped cell culture of the present disclosure can be used in combination with a component for enhancing the viability, engrafting property and/or functions of the high-purity cell population and/or sheet-shaped cell culture, or other effective component useful for treatment of the disease to be treated.

A further aspect of the present disclosure relates to a medical composition containing an effective component selected from the group including the high-purity cell population of the present disclosure and the sheet-shaped cell culture of the present disclosure.

The medical composition of the present disclosure may contain, in addition to the high-purity cell population and/or sheet-shaped cell culture of the present disclosure, various additive components, examples of which include a carrier that is pharmaceutically acceptable, components for enhancing the viability, engrafting property and/or functions of the high-purity cell population and/or sheet-shaped cell culture, and other effective components useful for treatment of the disease to be treated. As such additive components, there can be used any known ones, and persons skilled in the art are well acquainted with these additive components. IN addition, the medical composition of the present disclosure can be used jointly with a component for enhancing the viability, engrafting property and/or functions of the high-purity cell population and/or sheet-shaped cell culture, or other effective component useful for treatment of the disease to be treated. In one embodiment, the medical composition of the present disclosure is for use in treating diseases associated with tissue abnormality. The tissues and diseases to be treated are as described above in relation to the high-purity cell population and sheet-shaped cell culture of the present disclosure.

Another aspect of the present disclosure relates to a kit (set or pack) which includes part or all of the elements to be used for production of the high-purity cell population, sheet-shaped cell culture or composition (for example, medical composition) of the present disclosure and which is for producing the high-purity cell population, sheet-shaped cell culture or composition (for example, medical composition) of the present disclosure, or for treating a disease (for example, diseases associated with tissue abnormality) (hereinafter, such a kit may be referred to as "the production kit of the present disclosure"). Herein, the terms "set" and "pack" are used interchangeably with "kit" and, hence, the descriptions related to the "kit" herein also apply to the "set" and the "pack."

Specific elements included in the kit of the present disclosure will be made clear by reference to the above descriptions related to the production of the high-purity cell population, sheet-shaped cell culture or medical composition or the like of the present disclosure, and, therefore, not all the elements are set forth here. In one embodiment, the kit of the present disclosure may include various elements, examples of which include, without restriction, an agent for changing a character of the contaminating cells (for example, an agent for conversion of cell species, an agent for marker expression or for inhibition of marker expression, an agent for conversion to iPS cells, an agent for inducing differentiation of iPS cells to other cell species, etc.), a cell population for use in production of the high-purity cell population (for example, a cell population isolated from a living body, etc.), cells for use in cultivating the sheet-shaped cell culture (for example, the high-purity cell population of the present disclosure, etc.), a culture liquid, a culture dish, a washing liquid, an agent for use in purification of the target cells and/or removal of the contaminating cells (for example, an antibody, a washing liquid, etc.), instruments (for example, pipette, dropping pipette, tweezers, beads, affinity column, filter, etc.), and instructions related to the production method and/or use method of the high-purity cell population, sheet-shaped cell culture or composition or the like (for example, an instruction book, a medium such as flexible disc, CD, DVD, Blu-ray Disc, memory card or USB memory on which information about the production method and/or use method is recorded, etc.).

In a specific embodiment, the kit for producing the high-purity cell population or composition containing the same of the present disclosure includes an agent for changing a character of the contaminating cells, and an agent for use in purification of the target cells and/or removal of the contaminating cells. In another specific embodiment, the kit for producing the high-purity cell population or composition containing the same of the present disclosure includes a cell population isolated from a living body, an agent for changing a character of the contaminating cells, and an agent for use in purification of the target cells and/or removal of the contaminating cells. In a further embodiment, the kit for producing the sheet-shaped cell culture or composition containing the same of the present disclosure includes the high-purity cell population of the present disclosure, a culture liquid and a culture dish. In another embodiment, the kit for producing the sheet-shaped cell culture or composition containing the same of the present disclosure includes a cell population isolated from a living body, an agent for changing a character of the contaminating cells, an agent for use in purification of the target cells and/or removal of the contaminating cells, a culture liquid and a culture dish.

A further aspect of the present disclosure relates to a method for treating a subject's disease, the method including a step of administering an effective amount of the high-purity cell population, sheet-shaped cell culture or medical composition of the present disclosure to the subject needing the same (hereinafter, such a method may be referred to simply as "treatment method"). The tissue and disease to be treated by the treatment method of the present disclosure are as described above in relation to the high-purity cell population and sheet-shaped cell culture of the present disclosure. In addition, in the treatment method of the present disclosure, components for enhancing the viability, engrafting property and/or functions or the like of the high-purity cell population and/or sheet-shaped cell culture, other effective components useful for treatment of the disease to be treated, or the like can be used jointly with the high-purity cell population, sheet-shaped cell culture or medical composition of the present disclosure.

The treatment method of the present disclosure may further include a step of producing the high-purity cell population, sheet-shaped cell culture or medical composition according to the production method of the present disclosure. The treatment method of the present disclosure may further include a step of collecting the whole blood, cells or a tissue as a source of cells for production of the high-purity cell population from a subject, prior to the step of producing the high-purity cell population, sheet-shaped cell culture or medical composition. In one embodiment, the subject from whom the whole blood and/or cells or a tissue as a source of cells is collected is the same individual as the subject to whom the high-purity cell population, sheet-shaped cell culture or medical composition is to be administered. In another embodiment, the subject from whom the whole blood and/or cells or a tissue as a source of cells is collected is the same species as, but is a different individual from, the subject to whom the high-purity cell population, sheet-shaped cell culture or medical composition is to be administered. In a further embodiment, the subject from whom the whole blood and/or cells or a tissue as a source of cells is collected is an individual of a different species from the subject to whom the high-purity cell population, sheet-shaped cell culture or medical composition is to be administered.

In the present disclosure, the subject may be healthy or may be suffering from some disease. In the case where it is planned to treat a disease, the subject typically means a subject suffering from the disease or a subject having a risk of contracting the disease.

In addition, the term "treatment" includes all kinds of medically acceptable preventive and/or curative interventions aimed at cure, temporary remission or prevention of a disease. For instance, the term "treatment" includes medically acceptable interventions for various purposes, such as slowing down or stopping the progress of a disease, causing retraction or disappearance of a lesion, and preventing onset of a disease or preventing recurrence of a disease.

In the present disclosure, an effective amount refers, for example, to an amount (for example, the number of cells contained in the high-purity cell population, sheet-shaped cell culture or medical composition, the size or weight of the sheet-shaped cell culture) making it possible to inhibit onset or recurrence of a disease, to alleviate a symptom, or to slow down or stop the disease progression, and is preferably such an amount as to prevent the onset or recurrence of the disease or to cure the disease. In addition, the effective amount is preferably such an amount as not to produce an adverse influence in excess of the advantageous effect of administration. Such an amount can be appropriately determined by, for example, tests performed using laboratory animals or disease model animals such as mice, rats, dogs and pigs, and the methods for such tests are well known to those skilled in the art. Besides, the size of a tissue lesion to be treated can be an important index for determination of the effective amount.

The high-purity cell population, sheet-shaped cell culture or medical composition of the present disclosure can be administered by way of a variety of routes such as intravenous, intramuscular, subcutaneous, local, intraarterial, intraportal, intraventricular, and intraperitoneal routes. In the case of the sheet-shaped cell culture or medical composition containing the same, the administration method may be, for example, direct application to the tissue. In addition, in the case of using fragments of the sheet-shaped cell culture, the fragments may be administered by way of various routes suited to administration by injection, such as intravenous, intramuscular, subcutaneous, local, intraarterial, intraportal, intraventicular, and intraperitoneal routes.

The frequency of administration is typically once per treatment; when this is not enough to obtain a desired effect, however, the administration may be carried out multiple times.

Example 1

Purification of Skeletal Myoblasts by Conversion of Fibroblasts into Fat Cells A cell suspension of a cell population isolated from a skeletal muscle is seeded onto a cell culture plate in a quantity of $0.8 \times 10^5$ cells/well, and is cultured overnight in a CO2 incubator. In a microtube is placed 30 μL of a serum-free culture medium, and 1.0 μg of PPARγ expression adenovirus vector (AdRGD-PPARγ, Gastroenterology. 2003 May; 124(5): 1315-24) is added thereto. The contents of the microtube are mixed by pipetting, then 5 μL of HilyMax solution (manufactured by Dojindo Laboratories) is added thereto, and the system is let stand still at room temperature for 15 minutes, to prepare an AdRGD-PPARγ-HilyMax complex. The AdRGD-PPARγ-HilyMax complex is added to the cultured cell population, and the plate is shaken gently. The cells are cultured in a CO2 incubator for 24 hours. The cell population is washed with PBS, followed by centrifugation, after which the cell population is seeded into a 80-cm2 flask in a density of 2 to $3 \times 10^4$ cells/cm2, and is cultured by use of 15 mL of culture medium (fat cell differentiation-inducing medium, manufactured by Cosmo Bio Co., Ltd.) for five to seven days. After the cultivation, the culture surface is washed with PBS, followed by a trypsin treatment, to obtain a cell population, which is filtered through a mesh (cell strainer, manufactured by Corning Incorporated) having a pore diameter of 70 μm, whereby the cell population having passed through the mesh is obtained as the desired cell population. The cell population thus obtained is labelled with anti-CD56 antibody, and the proportion of CD56-positive cells (skeletal myoblast purity) is measured by use of a flow cytometer.

The detailed description above describes a method of producing a cell population with a high target cell purity, a cell population obtained by the method, and a medical composition containing the cell population. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of producing a cell population with a high target cell purity, comprising:
    changing a character of contaminating cells in a cell population including target cells and the contaminating cells, the target cells being skeletal myoblasts, the contaminating cells being fibroblasts, and wherein the character is selected from the group consisting of cell shape, size, specific gravity, surface charge, adhesion potency, and marker, wherein the changing of the character of the contaminating cells comprises:
    converting the fibroblasts into fat cells, megakaryocytes, platelets, hepatocyte-like cells, macrophage-like cells, neurons, or cardiac muscle cells; and
    separating the fibroblasts from the skeletal myoblasts based on a difference in the cell size or the specific gravity of the fibroblasts and the skeletal myoblasts;
    removing the contaminating cells and/or collecting the target cells based on the changed characters; and
    culturing the target cells into a sheet shape.

2. The method according to claim 1, further comprising:
    performing a pretreatment, the pretreatment including a filtration, a centrifugation, or a separation between adhered cells and floating cells by an adhesion culture to separate the skeletal myoblasts and the fibroblasts from a tissue collected from a living body before the changing of the character of the contaminating cells in the cell population.

3. A method of producing a cell population with a high target cell purity, comprising:
    changing a character of contaminating cells in a cell population including target cells and the contaminating cells, the target cells being skeletal myoblasts, the contaminating cells being fibroblasts, and wherein the character is selected from the group consisting of cell shape, size, specific gravity, surface charge, adhesion potency, and marker, wherein the changing of the character of the contaminating cells comprises:
    converting the fibroblasts into fat cells; and
    separating the fibroblasts from the skeletal myoblasts based on a difference in the cell size or the specific gravity of the fibroblasts and the skeletal myoblasts;
    removing the contaminating cells and/or collecting the target cells based on the changed characters; and
    culturing the target cells into a sheet shape.

4. A method of producing a sheet-shaped cell culture, the method comprising:
    changing a character of contaminating cells in a cell population including target cells and the contaminating cells that is collected from a subject, the target cells being skeletal myoblasts, the contaminating cells being fibroblasts, and wherein the character is selected from the group consisting of cell shape, size, specific gravity, surface charge, adhesion potency, and marker, wherein the changing of the character of the contaminating cells comprises:
    converting the fibroblasts into fat cells, megakaryocytes, platelets, hepatocyte-like cells, macrophage-like cells, neurons, or cardiac muscle cells; and
    separating the fibroblasts from the skeletal myoblasts based on a difference in the cell size or the specific gravity of the fibroblasts and the skeletal myoblasts;
    obtaining a cell population with a high target cell purity by removing the contaminating cells and/or collecting the target cells based on the changed characters;
    freezing the cell population;
    thawing the frozen cell population;
    culturing the cell population into a sheet shape to form a sheet-shaped cell culture; and
    recovering the sheet-shaped cell culture formed.

5. The method according to claim 4, further comprising:
    performing a pretreatment, the pretreatment including a filtration, a centrifugation, or a separation between adhered cells and floating cells by an adhesion culture to separate the skeletal myoblasts and the fibroblasts from a tissue collected from a living body before the changing of the character of the contaminating cells in the cell population.

6. A method of producing a sheet-shaped cell culture, the method comprising:
    changing a character of contaminating cells in a cell population including target cells and the contaminating cells that is collected from a subject, the target cells being skeletal myoblasts, the contaminating cells being fibroblasts, and wherein the character is selected from the group consisting of cell shape, size, specific gravity, surface charge, adhesion potency, and marker, wherein the changing of the character of the contaminating cells comprises:
converting the fibroblasts into fat cells, megakaryocytes, platelets, hepatocyte-like cells, macrophage-like cells, neurons, or cardiac muscle cells; and
separating the fibroblasts from the skeletal myoblasts based on a difference in the cell size or the specific gravity of the fibroblasts and the skeletal myoblasts;
obtaining a cell population with a high target cell purity by removing the contaminating cells and/or collecting the target cells based on the changed characters;
freezing the cell population;
thawing the frozen cell population;
culturing the cell population into a sheet shape to form a sheet-shaped cell culture; and
recovering the sheet-shaped cell culture formed.

7. A method of producing a cell population with a high target cell purity, comprising:
changing a character of contaminating cells in a cell population including target cells and the contaminating cells, the target cells being skeletal myoblasts, the contaminating cells being fibroblasts, and wherein the character is selected from the group consisting of cell size or specific gravity;
removing the contaminating cells and/or collecting the target cells based on the changed character; and
culturing the target cells into a sheet shape.

8. The method according to claim 7, wherein the changing of the character of the contaminating cells comprises:
converting the fibroblasts into megakaryocytes, platelets, hepatocyte-like cells, macrophage-like cells, neurons, or cardiac muscle cells; and
separating the fibroblasts from the skeletal myoblasts based on a difference in the cell size of the fibroblasts and the skeletal myoblasts.

9. The method according to claim 7, wherein the changing of the character of the contaminating cells comprises:
converting the fibroblasts into fat cells; and
separating the fibroblasts from the skeletal myoblasts based on a difference in the specific gravity of the fibroblasts and the skeletal myoblasts.

\* \* \* \* \*